United States Patent [19]

Suhadolnik

[11] Patent Number: 5,144,075
[45] Date of Patent: Sep. 1, 1992

[54] PROCESS FOR THE PREPARATION OF N,N-DIHYDROCARBYLHYDROXYLA-MINES

[75] Inventor: Joseph Suhadolnik, Ossining, N.Y.

[73] Assignee: Ciba-Geigy Corporation, Ardsley, N.Y.

[21] Appl. No.: 642,619

[22] Filed: Jan. 17, 1991

[51] Int. Cl.$^5$ ................. C07C 239/08; C07C 239/10; C07C 239/12

[52] U.S. Cl. ..................................... 564/301; 564/300

[58] Field of Search .................. 564/300, 301, 259

[56] References Cited

U.S. PATENT DOCUMENTS

| 4,590,231 | 5/1986 | Seltzer et al. ...................... 524/100 |
| 4,668,721 | 5/1987 | Seltzer et al. ...................... 524/95 |
| 4,782,105 | 11/1988 | Ravichandran et al. ........... 524/236 |
| 4,876,300 | 10/1989 | Seltzer et al. ...................... 524/100 |
| 4,910,340 | 3/1990 | Marans et al. ...................... 564/301 |

FOREIGN PATENT DOCUMENTS 0517860 10/1955 Canada ................. 564/259
0102856 6/1982 Japan .
1134851 11/1968 United Kingdom .

OTHER PUBLICATIONS

Vavon et al. "Sur l'hydrogénation catalytique des oximes, etc" Bull. Soc. Chim. France, 43, 231–237 (1928).
R. F. Borch et al., J. Am. Chem. Soc., 93, 2897 (1971).
G. W. Gribble et al., Synthesis, 1977, 856.

Primary Examiner—Glennon H. Hollrah
Assistant Examiner—P. O'Sullivan
Attorney, Agent, or Firm—Luther A. R. Hall

[57] ABSTRACT

Symmetrically substituted N,N-dihydrocarbylhydroxylamines are prepared in a single step by the reaction of an aldehyde and hydroxylamine hydrochloride in an alcoholic solvent in the presence of hydrogen and a hydrogenation catalyst. The free N,N-dihydrocarbylhydroxylamine is liberated from the hydrochloride salt by treatment with alkali. N,N-dihydrocarbylhydroxylamines, particularly the N,N-dialkylhydroxylamines, are useful stabilizers for a variety of polymers.

9 Claims, No Drawings

PROCESS FOR THE PREPARATION OF N,N-DIHYDROCARBYLHYDROXYLAMINES

The instant invention pertains to a process for the preparation of N,N-dihydrocarbylhydroxylamines from an aldehyde and hydroxylamine hydrochloride under hydrogenation conditions in a facile, one-step method.

BACKGROUND OF THE INVENTION

N,N-Dihydrocarbylhydroxylamines, such as N,N-dialkylhydroxylamines and N,N-dibenzylhydroxylamine, are well known as useful stabilizers for a variety of polymeric substrates as is taught for example in U.S. Pat. Nos. 4,590,231; 4,668,721; 4,782,105 and 4,876,300.

A number of methods are known for the preparation of N,N-dialkylhydroxylamines, and are reviewed by S. R. Sandler and W. Karo in "Organic Function Group Preparations", Vol. 3, Academic Press, New York, 1972, Chapter 10. These methods include the direct oxidation of N,N-dialkylamines with aqueous hydrogen peroxide (U.S. Pat. No. 4,782,105); the metathesis reaction between an alkyl halide and a hydroxylamine in the presence of alkali; and the catalytic hydrogenation of nitrones (U.S. Pat. No. 4,910,340).

A method more germane to the instant invention is described by G. Vavon et al., Bull. Soc. Chim. France, 43, 231-237 (1928) wherein the catalytic hydrogenation of aldoximes using a platinum catalyst in wet ethanol in the presence of hydrochloric acid generates N,N-dialkylhydroxylamines via a reductive coupling reaction. Thus, heptaldehyde oxime formed N,N-diheptylhydroxylamine in excellent yield (90% unpurified), but benzaldehyde oxime gives a mixture of N,N-dibenzylhydroxylamine plus dibenzylamine.

The same reductive coupling of heptanal oxime or benzaldehyde oxime to N,N-diheptylhydroxylamine or N,N-dibenzylhydroxylamine is reported by R. F. Borch et al., J. Am. Chem. Soc., 93, 2897 (1971) using cyanohydridoborate anion as a selective reducing agent.

G. W. Gribble et al., Synthesis, 1977, 856 teach the preparation of N,N-dialkylhydroxylamine by a similar reductive coupling reaction using an aldehyde oxime with sodium borohydride in an acid media. N,N-Di-n-butylhydroxylamine is prepared by reacting butanal oxime with sodium borohydride in acetic acid.

It is noted that in each of the reductive coupling reactions described supra, coupling produces a half equivalent of hydroxylamine as a byproduct which is either reduced to ammonia under the reaction conditions or remains as a contaminant in the desired N,N-dialkylhydroxylamine main product.

The instant process overcomes this disadvantage and additionally provides several advantages of its own. The instant starting materials are readily available aldehydes and inexpensive readily available hydroxylamine hydrochloride. This allows for great flexibility in syntheses since a wide variety of aldehydes are accessible and there is no need to isolate any intermediates such as the oximes.

More importantly from an economic and environmental point of view, since an oxime is not a starting material, only one half equivalent of hydroxylamine hydrochloride relative to the aldehyde is really required by the overall stoichiometry of the process.

Accordingly, the instant process can be carried out in such a way that no hydroxylamine byproduct is produced.

DETAILED DISCLOSURE

Symmetrically substituted N,N-dihydrocarbylhydroxylamines are prepared in a single step by the reaction of an aldehyde and hydroxylamine hydrochloride in an alcoholic solvent in the presence of hydrogen and a hydrogenation catalyst. The free N,N-dihydrocarbylhydroxylamine is liberated from the hydrochloride salt by treatment with alkali.

The instant invention pertains to a process for the preparation of a symmetrically substituted N,N-dihydrocarbylhydroxylamine of formula I $$(RCH_2)_2NOH \qquad (I)$$

wherein

R is straight or branched chain alkyl of 1 to 17 carbon atoms, said alkyl substituted by phenyl, cycloalkyl of 5 to 12 carbon atoms, aryl of 6 to 10 carbon atoms or said aryl substituted by one or two alkyl of 1 to 12 carbon atoms, which process comprises reacting at ambient temperature
(a) an aldehyde RCHO, where R is defined above, and
(b) from 0.5 to 1.0 equivalents of hydroxylamine hydrochloride per each equivalent of RCHO, reactants (a) and (b), being dissolved in an organic solvent which is or contains a major portion of a lower alkanol, under an atmosphere of hydrogen at 15-60 psi (1.05-4.2 Kg/cm$^2$) pressure in the presence of a catalytically effective amount of a noble metal hydrogenation catalyst till hydrogen uptake is complete, and isolating the desired N,N-dihydrocarbylhydroxylamine of formula I from its hydrochloride salt using alkali.

Preferably, R is alkyl of 2 to 15 carbon atoms, 2-phenylethyl, cycloalkyl, phenyl, tolyl or xylyl. Most preferably, R is n-amyl, n-undecyl or n-pentadecyl.

When R is alkyl, it is, for example, methyl, ethyl, n-butyl, isobutyl, n-amyl, isoamyl, 2-ethylhexyl, n-hexyl, n-octyl, undecyl or n-heptadecyl. When R is cycloalkyl, it is, for example, cyclopentyl, cyclohexyl, cyclooctyl or cyclododecyl. When R is alkyl substituted by phenyl, it is, for example, benzyl or 2-phenylethyl. When R is aryl, it is, for example, phenyl or naphthyl. When R is phenyl substituted with alkyl, it is, for example, tolyl or xylyl.

In the instant process, 0.5 to 1.0 equivalents of hydroxylamine hydrochloride for each equivalent of aldehyde are added to a solution of said aldehyde to form the corresponding oxime in situ. The solution is agitated under an atmosphere of hydrogen at 15 to 60 psi (1.05-4.2 Kg/cm$^2$) pressure at ambient temperature till the uptake of hydrogen is complete. This normally takes from 30 minutes to 12 hours depending on the particular aldehyde being used in the process. The hydrochloride salt of the N,N-dihydrocarbylhydroxylamine is formed as the product of the reactions set forth below. The free N,N-dihydrocarbylhydroxylamine is liberated from the hydrochloride salt by conventional treatment with aqueous alkali.

The hydroxylamine hydrochloride regenerated upon the reductive coupling of the two molecules of oxime (see second equation above) is free under reaction conditions to condense with any remaining aldehyde to form more oxime in situ. This oxime can then reductively couple allowing for complete conversion of aldehyde to N,N-dihydrocarbylhydroxylamine when as little as half of an equivalent of hydroxylamine hydrochloride is used per equivalent of aldehyde as starting material in the instant process.

When hydrogen uptake is complete, normally about 30 minutes to 12 hours, the catalyst is removed by filtration. The filtrated is evaporated to remove the solvent present and the residue is treated with aqueous alkali, e.g. aqueous potassium carbonate solution, to liberate the free N,N-dihydrocarbylhydroxylamine. If the product is a solid, it is isolated by filtration and purified by recrystallization, Alternatively, the product can be isolated by extraction of the alkaline solution with an organic solvent, such as ethyl acetate or methylene chloride, and purified by conventional means if necessary. Examination of the crude products of the instant process by $^1$H NMR data reveals that said products are typically better than 90% pure and that further purification by recrystallization etc may not be necessary.

The aldehydes used in the instant process are items of commerce or are readily prepared by known methods. Hydroxylamine hydrochloride is an item of commerce as well.

Typical solvents used in the process are the lower alkanols, i.e. methanol, ethanol, isopropanol, propanol, and methanol/ethyl acetate mixtures, methanol/methylene chloride mixtures, ethanol/ethyl acetate mixtures and alkanol/tetrahydrofuran mixtures.

The equivalent or mole ratio of aldehyde to hydroxylamine hydrochloride is 1:0.5 to 1:1; preferably 1:0.5 to 1:0.6.

Typical noble metal hydrogenation catalysts used in the instant process are 5% platinum on carbon, 10% platinum on carbon, platinum oxide, a combination of 5% platinum on carbon with platinum oxide and 5% palladium on carbon. The catalytically effective amount of catalyst is 0.1 to 1 molar percently, preferably 0.15 to 0.25 molar percent, based on the aldehyde RCHO. A platinum catalyst is preferred.

The hydrogenation of oximes in general and the reductive coupling reactions described in prior art are usually slower, unpredictable and non-specific in the absence of acid. In the instant process, the hydrogen chloride introduced via the hydroxylamine hydrochloride salt starting material is quite sufficient to make the instant process go smoothly and with specificity. The addition of more acid is unnecessary in the instant process.

The instant process is distinguished particularly by requiring only about a half equivalent of hydroxylamine hydrochloride per equivalent of aldehyde compared to the process of the prior art. As a result, there is no NH$_2$OH generated as a by-product in the instant process and isolation and purification of the desired hydroxylamine product is facilitated which represent clear economic advantages for the instant process.

The N,N-dialkylhydroxylamines made by the instant process are effective stabilizers for polyolefins and other polymer substrates.

The following examples are presented for the purpose of illustration only and are not to be construed to limit the nature or scope of the instant invention in any manner whatsoever.

EXAMPLE 1

N,N-Di-n-propylhydroxylamine

A solution of propanal (5.0 g, 86.2 mmol) and hydroxylamine hydrochloride (6.3 g, 90 mmol) in 100 ml of methanol is shaken under hydrogen at 40–45 psi (2.8–3.15 Kg/cm$^2$) in the presence of a catalytic amount of 5% platinum on carbon (400 mg) and platinum oxide (10 mg) for 2.5 hours at room temperature. The mixture is then filtered through CELITE filter agent. The filtrate is concentrated and the residue partitioned between ethyl acetate and saturated aqueous potassium carbonate solution. The organic layer is washed with water and brine, dried over anhydrous sodium sulfate and then concentrated to give 3.8 g of N,N-di-n-propylhydroxylamine contaminated with a minor amount of ethyl acetate as shown by 90 MHz $^1$H NMR. A purified analytical sample is obtained by flash chromatography on silica gel (4:1:: hexane:ethyl acetate).

$^1$H NMR (200 MHz, CDCl$_3$) δ2.63 (dd, 4H's); 1.61 (sextet, 4H's); 0.92 (t, 6H's).

IR (CDCl$_3$) 3560, 3240 (broad), 2960, 2920, 2860, 1440, 1120, 1050 cm$^{-1}$.

EXAMPLE 2

N,N-Di-n-hexylhydroxylamine

A solution of hexanal (5.0 g, 50 mmol) and hydroxylamine hydrochloride (3.8 g, 55 mmol) in 60 ml of methanol is shaken under hydrogen at 40–45 psi (2.8–3.15 Kg/cm$^2$) for two hours at room temperature in the presence of a catalytic amount of 5% platinum on carbon (400 mg). The reaction mixture is then treated following the procedure given in Example 1 to give 4.2 g of crude N,N-di-n-hexylhydroxylamine product as a white solid. The product is identified by 90 MHz $^1$H NMR and is seen to be contaminated with no more than 5% of hexanal oxime.

An analytically pure sample of the desired N,N-di-n-hexylhydroxylamine product is obtained by flash chromatography on silica gel (6:1:: heptane:ethyl acetate) to give 2.5 g (50% overal yield) of the title compound as a white solid melting at 67° C.

$^1$H NMR (200 MHz, CDCl$_3$) δ2.68 (dd, 4H's); 1.60 (quintet, 4H's); 1.30 (broad, 12H's); 0.88 (t, 6H's).

IR (CDCl$_3$) 3570, 3200 (broad), 2920, 2820, 1440, 1120, 1070 cm$^{-1}$.

EIMS, m/z 201 (M+).

Analysis: Calcd. for C$_{12}$H$_{27}$NO: C, 71.6; H, 13.5; N, 7.0. Found: C, 71.8; H, 13.9; N, 6.8.

EXAMPLE 3

N,N-Di-n-hexylhydroxylamine

Following the general procedure of Example 2, hexanal (5.0 g, 50 mmol) is reacted with only one half equivalent of hydroxylamine hydrochloride (1.9 g, 28 mmol) to give 3.4 g of crude N,N-di-n-hexylhydroxylamine as a white solid which 90 $^1$H NMR confirmed to be essentially only one compound. Purification of the crude product as described in Example 2 gives 2.0 g of the title compound as a white solid melting at 67° C.

This example shows that the instant process using only a half equivalent of hydroxylamine hydrochloride per equivalent of aldehyde affords the desired N,N-dialkylhydroxylamine in high yield and better purity without the concomitant preparation of undesired byproducts.

EXAMPLE 4

N,N-Di-n-dodecylhydroxylamine

A solution of dodecanal (9.2 g, 50 mmol) and hydroxylamine hydrochloride (3.8 g, 54 mmol) in 75 ml of methanol and 10 ml of ethyl acetate is shaken under hydrogen at 40–45 psi (2.8–3.15 Kg/cm$^2$) for five hours at room temperature in the presence of a catalytic amount of 5% platinum on carbon (450 mg). The reaction mixture is then filtered through CELITE filter agent. The filtrate is concentrated and the residue is treated with a saturated aqueous potassium carbonate solution till the pH is over 10. A white solid is isolated by filtration and is recrystallized from methanol to provide 4.7 g (51% yield) of the title compound as a white solid melting at 88° C.

$^1$H NMR (90 MHz. CDCl$_3$) δ2.6 (dd, 4H's); 1.6 (m, 4H's); 1.3 (broad, 36H's); 0.9 (t, 6H's).

IR (CDCl$_3$) 3540, 3150 (broad), 2920, 2820, 1440, 1130 cm$^{-1}$.

EIMS, m/z 369 (M+).

EXAMPLE 5

N,N-Di-n-dodecylhydroxylamine

A solution of dodecanal (9.2 g, 50 mmol) and hydroxylamine hydrochloride (2.0 g, 29 mmol) in 70 ml of methanol and 10 ml of ethyl acetate is shaken under hydrogen at 40–45 psi (2.8–3.15 Kg/cm$^2$) for 2.5 hours at room temperature in the presence of a catalytic amount of 5% platinum on carbon (400 mg) and platinum oxide (15 mg). The reaction mixture is then worked up as described in Example 4 to give, after recrystallization from methanol, 4.6 g (50% yield) of the title compound as a white solid identical to that prepared in Example 4.

This example also demonstrates that the instant process using only a half equivalent of hydroxylamine hydrochloride per equivalent of aldehyde affords the desired N,N-dialkylhydroxylamine in good yield and purity without the undesired concomitant preparation of unwanted byproducts.

EXAMPLE 6

N,N-Di-n-hexadecylhydroxylamine

Following the general procedure of Example 5, a solution of hexadecanal (2.5 g, 10.4 mmol) in 15 ml of tetrahydrofuran is added to a solution of hydroxylamine in hydrochloride (0.45 g, 6.4 mmol) in 10 ml of methanol and 4 ml of water. The resulting mixture is shaken under hydrogen at 40–45 psi (2.8–3.15 Kg/cm$^2$) for two hours at ambient temperature in the presence of a catalytic amount of a platinum catalyst. The mixture is filtered through CELITE filter agent and the filtrate concentrated. The residue is partitioned between methylene chloride and saturated aqueous potassium carbonate. The organic layer is washed with water and brine, dried over anhydrous sodium sulfate and concentrated to give 1.9 g of a white solid containing the title compound as evidenced by 90 MHz $^1$H NMR.

What is claimed is:

1. An improved process for the preparation of a symmetrically substituted N,N-dihydrocarbylhydroxylamine of formula I

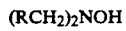    (1)

wherein

R is straight or branched chain alkyl of 1 to 17 carbon atoms, said alkyl substituted by phenyl, cycloalkyl of 5 to 12 carbon atoms, aryl of 6 to 10 carbon atoms or said aryl substituted by one or two alkyl of 1 to 12 carbon atoms, wherein the improvement comprises reacting at ambient temperature (a) an aldehyde RCHO, where R is defined above, and (b) from 0.5 to 0.6 equivalents of hydroxylamine hydrochloride per each equivalent of RCHO, reactants (a) and (b), being dissolved in an organic solvent which is or contains a major portion of a lower alkanol, under an atmosphere of hydrogen at 15'60 psi (1.05–4.2 Kg/cm$^2$) pressure in the presence of a catalytically effective amount of a noble metal hydrogenation catalyst till hydrogen uptake is complete, and isolating the desired N,N-dihydrocarbylhydroxylamine of formula I from its hydrochloride salt using alkali.

2. A process according to claim 1 wherein R is alkyl of 2 to 15 carbon atoms, 2-phenylethyl, cycloalkyl, phenyl, tolyl orxylyl.

3. A process according to claim 2 wherein R is n-amyl, n-undecyl or n-pentadecyl.

4. A process according to claim 1 wherein the product of formula I is N,N-di-n-propylhydroxylamine.

5. A process according to claim 1 wherein the product of formula I is N,N-di-n-hexylhydroxylamine.

6. A process according to claim 1 wherein the product of formula I is N,N-di-n-dodecylhydroxylamine.

7. A process according to claim 1 wherein the product of formula I is N,N-di-n-hexadecylhydroxylamine.

8. A process according to claim 1 wherein the catalytically effective amount of the noble metal catalyst is 0.1 to 1 molar percent based on the aldehyde RCHO.

9. A process according to claim 8 wherein the noble metal catalyst is a platinum catalyst.

* * * * *